United States Patent [19]

Odanaka

[11] Patent Number: 5,307,810
[45] Date of Patent: May 3, 1994

[54] DIAGNOSIS DEVICE WITH FUNCTION FOR ANGLING TIP PROBE

[75] Inventor: Kunio Odanaka, Tokyo, Japan

[73] Assignee: Kabushiki Kaisha Machida Seisakusho, Tokyo, Japan

[21] Appl. No.: 978,759

[22] Filed: Nov. 19, 1992

[30] Foreign Application Priority Data

Dec. 6, 1991 [JP] Japan .................................. 3-348514

[51] Int. Cl.⁵ .............................................. A61B 8/00
[52] U.S. Cl. ............................ 128/662.03; 128/662.06; 128/772
[58] Field of Search ..................... 128/662.03, 662.06, 128/772, 773, 4; 604/280

[56] References Cited

U.S. PATENT DOCUMENTS

| | | | |
|---|---|---|---|
| 4,349,032 | 9/1982 | Koyata | 128/662.06 |
| 4,489,728 | 12/1984 | Matsuo et al. | 128/4 |
| 4,558,706 | 12/1985 | Nakada et al. | 128/4 |

FOREIGN PATENT DOCUMENTS

| | | | |
|---|---|---|---|
| 58-157434 | 9/1983 | Japan | 128/660.01 |
| 2-71508 | 5/1990 | Japan | 128/660.01 |

Primary Examiner—Kyle L. Howell
Assistant Examiner—George Manuel
Attorney, Agent, or Firm—Fish & Richardson

[57] ABSTRACT

A diagnosis device which includes a probe provided at a front end of an elongate insertion portion, and has the function of angling this probe. An angle portion is provided between the insertion portion and the probe, and the angle portion includes a pair of tubular segments pivotally connected together. The pair of segments are connected to the front end of the insertion portion and the rear end of the probe, respectively. A soft protective tube is disposed inside the pair of segments at the angle portion. An operating member is connected at one end thereof to a manipulation mechanism mounted on a body, and is connected at the other end thereof to the front segment of the angle portion. The operating member is disposed outside the protective tube at the angle portion.

8 Claims, 3 Drawing Sheets

DIAGNOSIS DEVICE WITH FUNCTION FOR ANGLING TIP PROBE

BACKGROUND OF THE INVENTION

This invention relates to a diagnosis device capable of angling a tip probe.

For example, an ultrasonic diagnosis device for a medical use, as disclosed in Japanese Laid-Open Patent Application No. 58-157434, comprises a body, an insertion portion extending from the body, and a probe mounted on a front end of the insertion portion through an angle portion, the probe having an ultrasonic oscillator. An internal structure of the angle portion comprises a row of cylindrical segments pivotally connected together. A manipulation member is provided on the body, and when this manipulation member is operated, an operating force is transmitted to the angle portion through an operating wire to bend the angle portion arcuately, thereby directing the probe in a desired direction.

One example of the use of the above ultrasonic diagnosis device will now be described. First, a trocar is inserted from a hole formed in a skin tissue of a human body, and the insertion portion of the ultrasonic diagnosis device is inserted into this trocar in such a manner that its probe is projected from the front end of the trocar to be located at an internal organ to be examined. Then, the manipulation member is operated to bend the angle portion to bring the ultrasonic oscillator of the probe into contact with the internal organ. In this condition, ultrasonic waves are emitted from the ultrasonic oscillator, and the ultrasonic oscillator receives the ultrasonic waves, reflected by the internal organ, and converts them into an electrical signal. This electrical signal is fed to a controller via a signal transmission cable passed through the angle portion and the insertion portion.

In the case of the above ultrasonic diagnosis device, in order to prevent a body fluid from contacting the signal transmission cable, the insertion portion and the angle portion are of a sealed construction. More specifically, the insertion portion comprises a metal tube. The angle portion includes a protective tube of a soft resin mounted around the above-mentioned row of segments.

In the above diagnosis device, when the insertion portion is withdrawn from the trocar after the diagnosis, with the angle portion kept bent, the protective tube of the angle portion be caught by the edge of the front end of the trocar and can be damaged.

Japanese Laid-Open Utility Model Application No. 2-71508 discloses an ultrasonic diagnosis device comprising another prior art device. In this diagnosis device, an ultrasonic oscillator is pivotally supported within an open front end portion of an insertion portion comprising a rigid tube. A wire is passed through the insertion portion, and is connected at its front end to the ultrasonic oscillator. By pulling the rear end of this wire, the ultrasonic oscillator is pivotally moved. The open front end portion of the insertion portion is closed by an elastic member, and this elastic member is deformed in response to the pivotal movement of the ultrasonic oscillator.

SUMMARY OF THE INVENTION

It is an object of this invention to provide a diagnosis device in which a protective tube of an angle portion will not be damaged.

According to the present invention, there is provided a diagnosis device comprising:
(a) a body;
(b) a hollow insertion portion extending from the body;
(c) an angle portion provided at a front end of the insertion portion, the angle portion comprising a pair of front and rear segments of a tubular shape which are pivotally connected together, and the rear segment being connected to the front end of the insertion portion;
(d) a rigid probe mounted on a front end of the angle portion, the front segment being connected to a rear end portion of the probe;
(e) manipulation means mounted on the body;
(f) an operating member received in the insertion portion and extending along a length of the insertion portion, a rear end of the operating member being connected to the manipulation means, and a front end of the operating member being substantially connected to the front segment of the angle portion; and
(g) a soft protective tube disposed inside the pair of segments at the angle portion, the operating member being disposed outside the protective tube.

BRIEF DESCRIPTION OF THE DRAWINGS

FIG. 2 is an enlarged cross-sectional view of an angle portion of the diagnosis device;

FIG. 3 is a partial cross-sectional, enlarged plan view of the angle portion;

FIG. 4 is a cross-sectional view taken along the line IV—IV of FIG. 2;

DETAILED DESCRIPTION OF THE PREFERRED EMBODIMENTS

Figure 1:
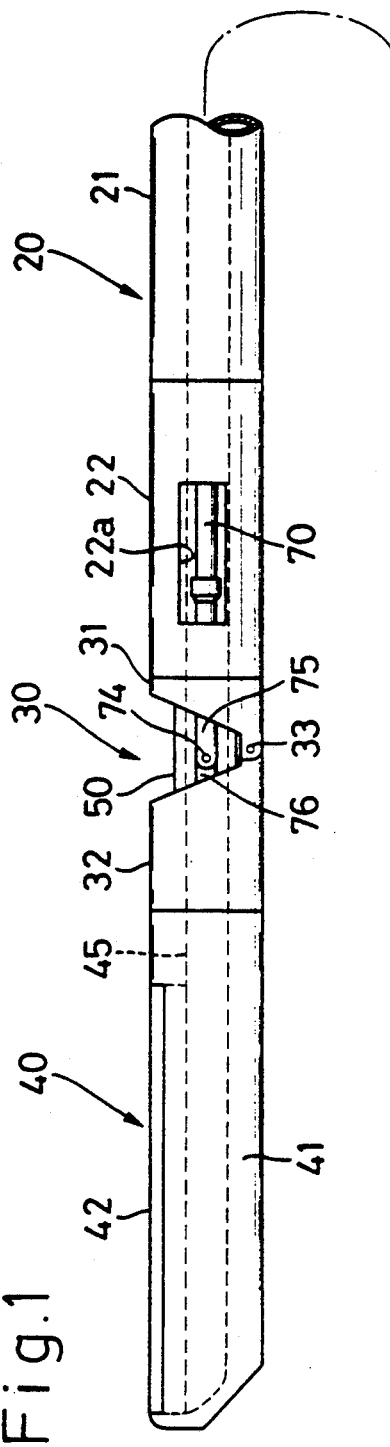
FIG. 1 is a partial cross-sectional, side-elevational view of the whole of a diagnosis device according to the present invention.
Figure 1:
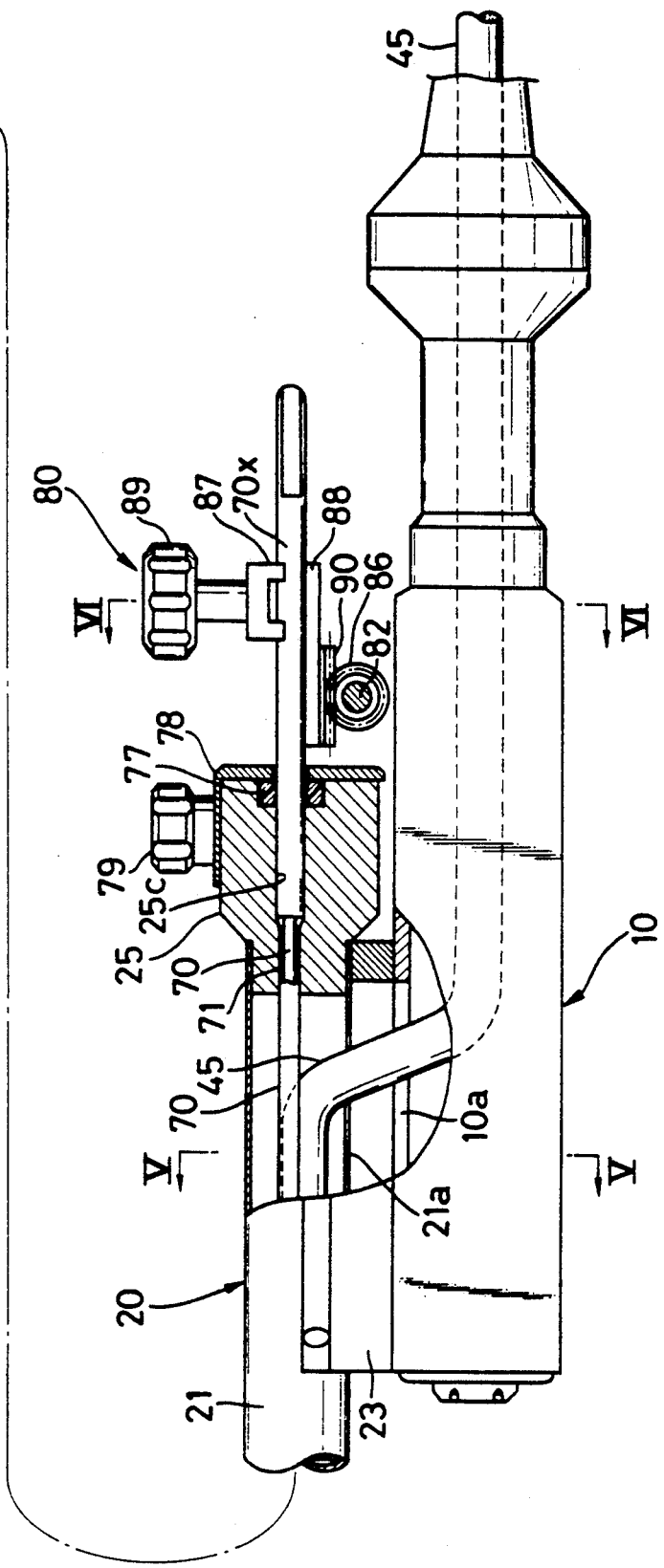

A preferred embodiment of the present invention will now be described with reference to the drawings. As shown in FIG. 1, an ultrasonic diagnosis device comprises a body 10, an insertion portion 20 extending from the body 10, an angle portion 30 mounted on a front end of the insertion portion 20, and a probe 40 mounted on a front end of the angle portion 30.

Figure 5:
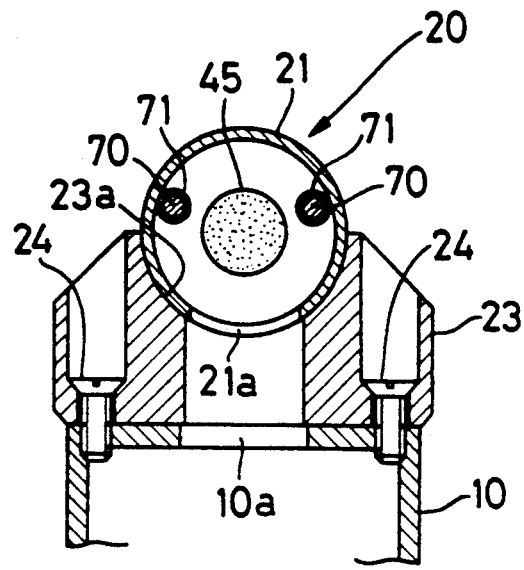
FIG. 5 is a cross-sectional view taken along the line V—V of FIG. 1.
Figure 6:
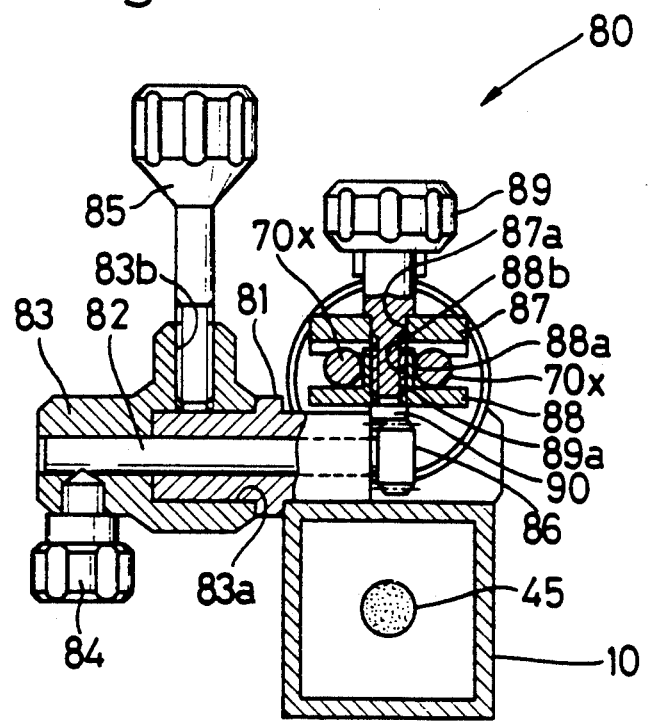
FIG. 6 is a partial cross-sectional view taken along the line VI—VI of FIG. 1.

As shown in FIGS. 1, 5 and 6, the body 10 is elongate and hollow, and has a rectangular parallelepipedic shape.

As shown in FIG. 1, the insertion tube 20 comprises a rigid tube 21, and a short rigid tube 22 connected to a front end of the rigid tube 21. The short tube 22 and the rigid tube 21 have the same diameter. The rear end portion of the rigid tube 21 is parallel to the body 10, and is fixedly secured to an upper wall of the body 10. More specifically, as shown in FIG. 5, the lower portion of the rear end portion of the rigid tube 21 is received in and fixedly secured to a recess 23a in a mounting member 23 which is fixedly secured to the upper wall of the body 10 by screws 24.

Figures 2, 3, 4:
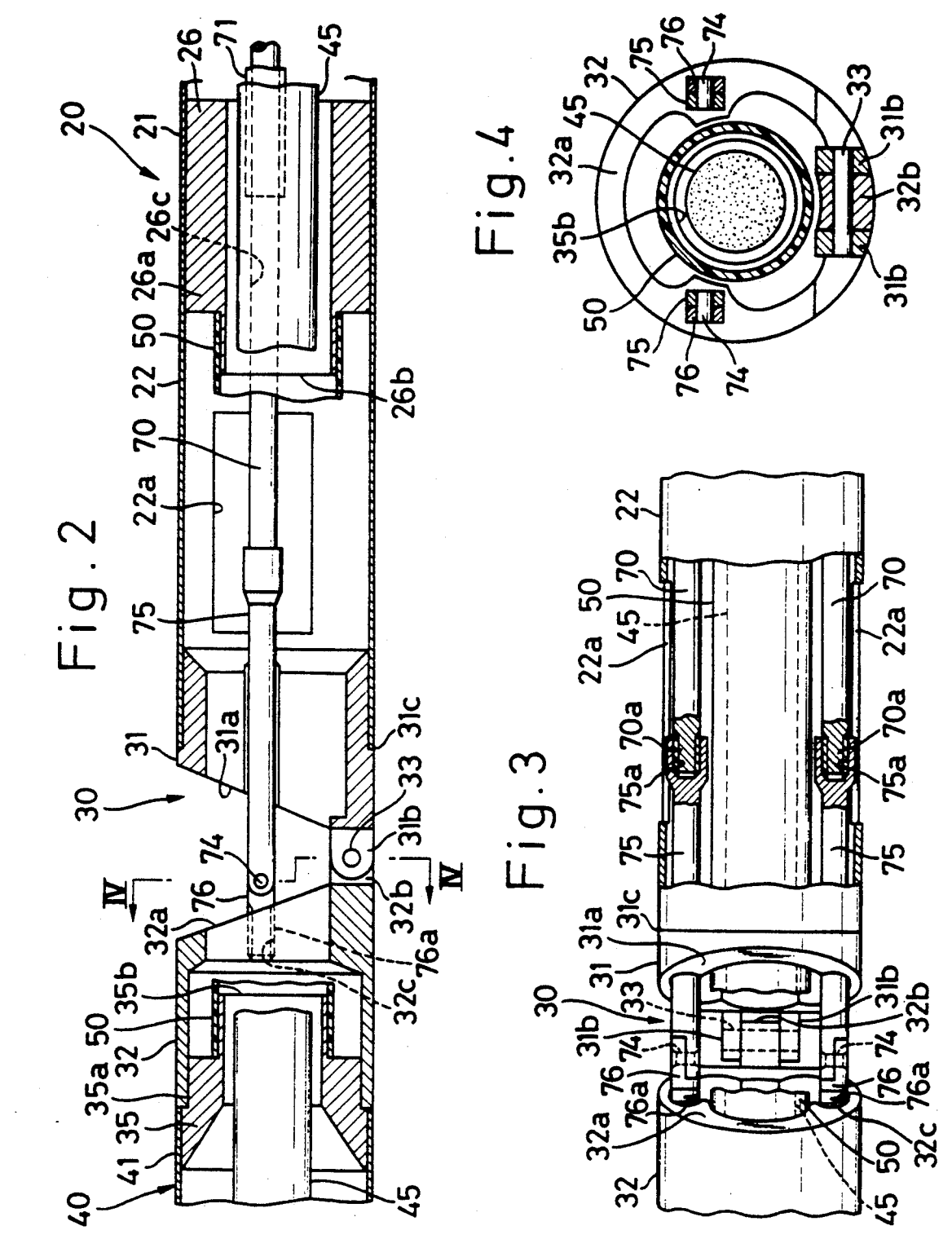

As shown in FIG. 1, a front end portion of a support member 25 is inserted into and fixed to the rear end of the rigid tube 21 to close this rear end. As shown in FIG. 2, the rear end of the short tube 22 is coaxially connected to the front end of the rigid tube 21 through a support member 26. The support member 26 includes a cylindrical base portion 26a, and a mounting portion 26b which extends forwardly from the base portion 26a, and is smaller in diameter than the base portion 26a. The rear end portion of the base portion 26a is inserted into and fixed to the front end portion of the rigid tube 21, and the rear end portion of the short tube 22 is fixedly mounted on the outer periphery of the front end portion of the base portion 26a. The support member 26 closes the open front end of the rigid tube 21. The support functions of these support members 25 and 26 will be described later.

As shown in FIG. 1, the probe 40 comprises a hollow base 41 of a rigid material, and an ultrasonic oscillator 42 which is mounted on the base 41, and is exposed to the exterior. The rear end portion of the base 41 has a hollow cylindrical shape.

As shown in FIGS. 1 to 4, the angle portion 30 comprises a pair of hollow cylindrical segments 31 and 32. Opposed surfaces of the segments 31 and 32 have respective inclined surfaces 31a and 32a which are inclined away from each other from specified portions thereof, and projections 31b and 32b are formed on these specified portions, respectively. The projections 31b and 32b are connected by a pin 33, thereby pivotally connecting the segments 31 and 32 together.

The rear segment 31 has an annular step 31c formed on the outer peripheral surface thereof, and a smaller-diameter portion of this segment 31 disposed rearwardly of this step 31c is inserted into and fixed to the front end portion of the short tube 22. That portion of the segment 31 disposed forwardly of the step 31c is projected from the front end of the short tube 22, and has an outer diameter equal to the outer diameter of the rigid tube 21 and the short tube 22.

As shown in FIGS. 2 and 4, the front segment 32 is connected to the probe 40 through a support member 35. More specifically, the support member 35 has a tubular base portion 35a, and a mounting portion 35b of a cylindrical shape which extends rearwardly from the base portion 35a in coaxial relation thereto, and is smaller in diameter than the base portion 35a. The rear end portion of the base 41 of the probe 40 is fixedly mounted on the outer periphery of the front end portion of the base portion 35a, and the front end portion of the segment 32 is fixedly mounted on the outer periphery of the rear end portion of the base portion 35a. The rear end portion of the base 41 is equal in outer diameter to the segment 32.

A front end portion of a protective tube 50, made of a soft resin, is mounted on the mounting portion 35b of the support member 35. The protective tube 50 is passed through the segments 32 and 31 of the angle portion 30 and the short tube 22, and is mounted at its rear end portion on the mounting portion 26b of the support member 26. The outer diameter of the protective tube 50 is smaller than the outer diameter of the segments 31 and 32.

A front end of a signal transmission cable 45 is connected to the ultrasonic oscillator 42 of the probe 40, and the signal transmission cable 45 is passed through the support member 35, the protective tube 50, the support member 26 and the rigid tube 21, and is further passed through holes 21a and 10a (see FIGS. 1 and 5), formed respectively in the peripheral wall of the rear end portion of the rigid tube 21 and the upper wall of the body 10, and the body 10, and is led out from the rear end of the body 10. The rear end of the signal transmission cable 45 is connected via a connector (not shown) to a controller (not shown) for receiving and transmitting electrical signals for ultrasonic vibration.

A manipulation mechanism 80 is mounted on the body 10. The manipulation mechanism 80 is connected to the angle portion 30 via a pair of operating rods 70, and the angle portion 30 is remotely operated by this manipulation mechanism 80.

The pair of operating rods 70 are passed through and guided by a pair of guide tubes 71, respectively. The guide tubes 71 are mounted within the rigid tube 21, and the rear end portions of the guide tubes 71 are supported by the support member 25, as shown in FIG. 1, and the front end portions thereof are supported by the support member 26, as shown in FIG. 2. More specifically, a pair of stepped through holes 25c are formed axially through the support member 25, and the rear end portion of each guide tube 71 is inserted in and fixed to the smaller-diameter front portion of a respective one of the through holes 25c. A pair of stepped through holes 26c are formed axially through the peripheral wall of the support member 26, and the front end portion of each guide tube 71 is inserted in and fixed to the larger-diameter rear end portion of a respective one of the through holes 26c. The right end of the through hole 25c is open to the outer surface of the support member 25. The left end of the through hole 26c is open to the front end surface of the support member 26, and is disposed outwardly of the protective tube 50.

Each operating rod 70 is connected at its front end to the front segment 32 of the angle portion 30 through links 75 and 76. More specifically, an externally-threaded portion 70a is formed on the front end portion of the operating rod 70, and this externally-threaded portion 70a is threaded into an internally-threaded portion 75a formed in the rear end portion of the link 75. The rear end of the link 76 is pivotally connected to the front end of the link 73 by a pin 74. An externally-threaded portion 76a is formed on the front end portion of the link 76, and this externally-threaded portion 76a is threaded into an internally-threaded portion 32c formed in the inclined surface 32a of the front segment 32. The positions of mounting of the pair of links 76 on the segment 32 are circumferentially spaced generally 90° from the projection 32b, and are spaced generally 180° from each other. When these operating rods 70 are pulled rearwardly, the probe 40 is pivotally moved about the pin 33 in a clockwise direction. In response to this pivotal movement of the probe 40, the link 76 is pivotally moved about the pin 74.

A pair of notches 22a are formed in the peripheral wall of the short tube 22, and each notch 22a is disposed in registry with the connected portions of the operating rod 70 and the link 75.

As shown in FIG. 1, the operating rod 70 has a rear end portion 70x of a larger diameter, and the front end portion of this larger-diameter portion 70x is slidably received in the rear end portion of the through hole 25c in the support member 25. The larger-diameter portion 70x of the operating rod 70 is projected from the rear end surface of the support member 25, and is releaseably connected to the manipulation mechanism 80. A seal ring 77 is received in the rear end portion of the through hole 25c in the support member 25 to seal a body fluid from leaking through a gap between the guide tube 71 and the operating rod 70. A holder plate 78 for holding the seal rings 77, received respectively in the pair of through holes 25c, are fixedly secured to the support member 25 by a bolt 79.

Next, the manipulation mechanism 80 will now be described with reference to FIGS. 1 and 6. As shown in FIG. 6, a base 81 is fixedly mounted on the upper surface of the body 10, and a shaft 82 is angularly movably extended through the base 81, the shaft 82 extending in a direction perpendicular to the longitudinal axes of the body 10 and the insertion portion 20. An attachment 83 is fixedly mounted on one end portion of the shaft 82 by a screw 84. The attachment 83 has a recess 83a which receives a cylindrical end portion of the base 81. A threaded hole 83b is formed through the peripheral wall of the attachment 83 defining the recess 83a, and extends radially of the attachment 83. One end portion of a lever 85 is threaded into the threaded hole 83b. A pinion 86 is fixedly mounted on the other end of the shaft 82.

The manipulation mechanism 80 further comprises a pair of upper and lower holder members 87 and 88 each in the form of a plate. The larger-diameter portions 70x of the pair of operating rods 70 are held between the holder members 87 and 88. More specifically, the upper holder member 87 has a through hole 87a extending vertically therethrough. The lower holder member 88 has a boss 88a projected upwardly, and a threaded hole 88b is formed in the boss 88a. A bolt 89 extends through the through hole 87a of the upper holder member 87, and a threaded portion 89a of this bolt 89 is threaded into the threaded hole 88b of the lower holder member 88. By tightening the bolt 89, the larger-diameter portions 70x of the pair of operating rods 70 are fixed to the holder members 87 and 88. A rack 90 extending along the length of the body 10 is fixedly secured to the lower surface of the lower holder member 88, and the pinion 86 is in mesh with the rack 90.

The operation of the above diagnosis device will now be described. The insertion portion 20 is inserted into a trocar (not shown) which has already been inserted into the body of the patient, and the angle portion 30 and the probe 40 are projected from the front end of the trocar, so that the probe 40 is disposed near an internal organ to be examined. Then, when the lever 85 is angularly moved in a direction perpendicular to the sheet of FIG. 6, the pinion 86 is angularly moved in the same direction through the attachment 83 and the shaft 82. As a result, the rack 90 in mesh with the pinion 86 is moved in the right direction in FIG. 1, so that the pair of operating rods 70 held between the holder members 87 and 88 are moved in the same direction. As a result, the segment 32 of the angle portion 30 and the probe 40 are pivotally moved in a clockwise direction (FIGS. 1 and 2), so that the ultrasonic oscillator 42 is brought into contact with the internal organ. In this condition, the lever 85 is threaded or driven home to abut its distal end against the outer peripheral surface of the base 81, thereby preventing the angular movement of the pinion 86 to maintain the inclined condition of the probe 40. In this condition, an electrical signal is fed from the controller to the ultrasonic oscillator 42 via the signal transmission cable 45, thereby causing the ultrasonic oscillator to produce ultrasonic vibrations. Then, the ultrasonic oscillator 42 receives the ultrasonic waves reflected by the internal organ, and converts them into an electrical signal, and this electrical signal is fed to the controller via the signal transmission cable 45.

When the above diagnosis is finished, the lever 85 is loosened to disengage its distal end from the outer peripheral surface of the base 81, and the lever 85 is angularly moved in a direction reverse to the above-mentioned direction. As a result, the operating rods 70 are moved in the left direction in FIG. 1, so that the segment 32 of the angle portion 30 and the probe 40 are pivotally moved in a counterclockwise direction to be brought into coaxial relation to the rigid tube 21. Then, the insertion is withdrawn from the trocar.

When trying to withdraw the insertion portion 20 from the trocar with the segment 32 of the angle portion 30 and the probe 40 kept inclined relative to the rigid tube 21, the front end of the trocar only strikes against the outer peripheral surface of the front segment 32, and will not be contacted with the protective tube 50 disposed inside the segments 31 and 32, and therefore damage to the protective tube 50 can be prevented.

After the insertion portion 20 is withdrawn from the trocar as described above, the ultrasonic diagnosis device is cleaned. The signal transmission cable 45 is received in the protective tube 50 and the rigid tube 21 in a sealed condition, and therefore does not need to be cleaned. The outer peripheral surface of the protective tube 50, the outer peripheral surface of the rigid tube 21, the inner and outer peripheral surfaces of the short tube 22 and the segments 31 and 32, and so on are cleaned.

Since the body fluid has intruded into the gap between each operating rod 70 and its mating guide tube 71, the outer peripheral surface of the operating rod 70 and the inner peripheral surface of the guide tube 71 need to be cleaned. Therefore, the bolt 89 is first loosened to release the rear end portion 70x of each operating rod 70 from the holder members 87 and 88, and the rear end portion 70x of the operating rod 70 is turned to release the threaded connection between the link 75 and the operating rod 70. This threaded condition or the released condition can be viewed through the notch 22a. Then, the operating rod 70 is withdrawn from the guide tube 71, and the outer peripheral surface of the operating rod 70 is cleaned, and the inner peripheral surface of the guide tube 71, as well as the inner peripheral surfaces of the through holes 25c and 26c of the support members 25 and 26, is cleaned by the use of a long brush.

It will be readily appreciated from the drawings that the manipulation mechanism 80 can be disassembled so that its parts can be cleaned independently of one another. It will also be readily understood that the seal ring 77 and the holder plate 78 can be removed for cleaning purposes.

The present invention is not limited to the above embodiment, and various modifications can be made without departing from the scope of the invention. For example, the use of the short tube 22 may be omitted, in which case the rear segment 31 may be made longer so that its rear end portion can be connected to the front end portion of the rigid tube 21 through the support member 26.

The rear segment may be formed integrally with the rigid tube of the insertion tube. The front segment may be formed integrally with the rear end portion of the base of the probe. The insertion portion may be flexible. The operating rods may be replaced by operating wires.

The operating rods or the operating wires may be disposed in diametrically opposite relation to the point of pivotal connection between the pair of segments. The probe may have an inspection window and an illumination window as in an endoscope, instead of the ultrasonic oscillator. The diagnosis device of the present invention can be used for industrial purposes.

What is claimed is:

1. A diagnosis device comprising:
   (a) a body;
   (b) a hollow insertion portion extending from said body;
   (c) an angle portion provided at a front end of said insertion portion, said angle portion comprising a pair of front and rear segments of a tubular shape which are pivotally connected together so that said front segment is rotatable relative to said rear segment about a rotation axis generally perpendicular to longitudinal axes of said pair of segments, said rear segment being connected to the front end of said insertion portions, and an outer periphery of at least said front segment of said angle portion being an exterior surface of said diagnosis device;
   (d) a rigid probe mounted on a front end of said angle portion, said front segment being connected to a rear end portion of said probe;
   (e) manipulation means mounted on said body;
   (f) an operating member received in said insertion portion and extending along a length of said insertion portion, a rear end of said operating member being connected to said manipulation means, and a front end of said operating member being substantially connected to said front segment of said angle portion; and
   (g) a soft protective tube received in said pair of segments at said angle portion, a portion of said operating member being disposed between said protective tube and said rear segment of said angle portion.

2. A diagnosis device according to claim 1, in which a first support member of a tubular shape is received in and fixed to the front end portion of said insertion portion, said probe having a tubular portion at its rear end portion, a second support member of a tubular shape being received in and fixed to said tubular portion, said first and second support members having respective tubular mounting portions disposed in opposed relation to each other, the diameter of said mounting portion of said first support member being smaller than the inner diameter of said insertion portion, the diameter of said mounting portion of said second support member being smaller than the inner diameter of said tubular portion of said probe, and opposite ends of said protective tube being connected to said mounting portions of said first and second support members, respectively.

3. A diagnosis device according to claim 2, in which there are provided a third support member fixedly mounted on a rear end portion of said insertion portion, and a guide tube for guiding said operating member, said first and third support members having respective through holes extending along an axis of said insertion portion, opposite ends of said guide tube being inserted in and fixed to said through holes of said first and third support members, respectively, said through hole of said first support member being open to a front end surface of said first support member, and being disposed outwardly of said protective tube, and an end of said through hole of said third support member is exposed to an exterior.

4. A diagnosis device according to claim 3, in which the front end of said operating member is releasably connected to said angle portion, and the rear end of said operating member being releaseably connected to said manipulation means.

5. A diagnosis device according to claim 4, in which said operating member is in the form of a rod, the front end of said operating member being connected to said front segment through first and second links, a rear end of said first link and the front end of said operating member being threadedly connected together, a front end of said first link and a rear end of said second link being pivotally connected together, and a front end of said second link being threaded into a rear end surface of said front segment.

6. A diagnosis device according to claim 5, in which said manipulation means comprises a pair of holder members, and a bolt which extends through one of said two holder members and is threaded into the other holder member, the rear end portion of said operating member being held between said pair of holder members.

7. A diagnosis device according to claim 1, in which said probe has an ultrasonic oscillator, there being provided a signal transmission cable which is connected at its front end to said ultrasonic oscillator and is passed through said protective tube, said insertion portion and said body to be led out to an exterior.

8. A diagnosis device according to claim 1, in which a pair of tubular mounting portions are mounted on a front end portion of said insertion portion and a rear end portion of said probe, respectively, said pair of tubular mounting portions being disposed in opposed relation to each other, the diameters of said pair of mounting portions being smaller than the inner diameters of said pair of segments, and opposite ends of said protective tube being connected to said pair of mounting portions, respectively.

* * * * *